United States Patent [19]

Weathers

[11] 4,440,755

[45] Apr. 3, 1984

[54] SPECIAL HEALING POWDER FOR LIVESTOCK

[76] Inventor: Edgar C. Weathers, 1801 S. 22nd St., Louisville, Ky. 40210

[21] Appl. No.: 529,274

[22] Filed: Sep. 6, 1983

Related U.S. Application Data

[63] Continuation-in-part of Ser. No. 69,598, Aug. 24, 1979, abandoned.

[51] Int. Cl.³ .............................................. A61K 33/18
[52] U.S. Cl. .................................................... 424/150
[58] Field of Search ........................................ 424/150

[56] References Cited

PUBLICATIONS

Thomas, Universal Formulary, Blanchard and Lea, Philadelphia, Pa. (1854), pp. 99–102, 155–157 and 431–432.

Stephenson et al., Veterinary Drug Encyclopedia and Therapeutic Index, Reuben H. Donnelley Corp., New York (1964), p. 111.

Pearson et al., Diseases of the Horse, U.S. Depart. of Agriculture (1923), pp. 405 and 479.

*Primary Examiner*—Richard Raymond
*Attorney, Agent, or Firm*—James R. Higgins, Jr.

[57] ABSTRACT

A composition for promoting the healing of a wound of an animal consisting of lime, alum and salt in selected proportions.

8 Claims, No Drawings

SPECIAL HEALING POWDER FOR LIVESTOCK

CONTINUATION-IN-PART APPLICATION

This is a continuation-in-part of my prior filed Application, Ser. No. 06/069598, filed Aug. 24, 1979, the disclosure in which is hereby incorporated by reference and which is now abandoned.

BACKGROUND OF THE INVENTION

In the field of veterinary medicine, particularly in the care of horses, certain ingredients are known for their healing propensities. For example, alum ($Al_2(SO_4)_3$) when combined and hydrated with potassium ($KAl(SO_4).12H_2O$) or ammonia ($NH_4Al(SO_4)_2.12H_2O$) is effective as an astringent in treating ulcerated surfaces. Generally, alum is thought to check bleeding and secretion from a wound.

In the field of caring for livestock, the effectiveness of alum to assist in curing flesh wounds is sometimes enhanced by the addition of other powdered materials, such as lime ($CaO$) or slaked lime ($Ca(OH)_2$). Lime is thought to act as a softener or liniment for the animal flesh, to permit the wound to heal more effectively, and salt is thought to act as an antiseptic.

Applicant has worked and cared for livestock, particularly horses, for a substantial number of years. Recently, coincident with the filing data of the original application, Applicant discovered a heretofore unknown combination of ingredients, hereinafter disclosed and described, which has proven surprisingly effective in treating flesh wounds of livestock, particularly horses.

DETAILED DESCRIPTION OF PREFERRED EMBODIMENT

The special healing powder herein disclosed uses powdered lime ($CaO$) as its primary component, in combination with selected proportions of powdered alum and granular salt which have been mixed together and well blended. While the individual components of the composition herein disclosed are previously known, when they are combined in the proportions and used in the manner herein described, the composition yields unexpected efficiency in promoting healing of flesh wounds.

The healing powder is made by dry-mixing and blending in the field using common measuring devices: one gallon of lime, more or less; one-half cup of alum, more or less; and one cup of salt, more or less. The basic proportion of ingredients of the composition herein disclosed is 91.43 volume percent powdered lime (one gallon), 2.86 volume percent powdered alum (one-half cup), and 5.71 volume percent salt (one cup), which have been dry-mixed together and well blended.

The ingredients are commonly commercially available in the form utilizable for the disclosed composition: powdered lime in bags or drums; powdered alum in bags or drums; and salt in granular form (even from the grocery store); iodized salt works equally as well as non-iodized. While the ingredients could be acquired in bulk form, the wide availability in powdered form makes powdered ingredients the logical choice to use in the first instance. A wide variety of mixing methods is likewise available to the user. Generally, stirring with even a crude stick would be effective, so long as the ingredients are well-blended. Obviously, more efficient means of mixing, such as a twin cone shell blender, would enhance the effectiveness of the mixing and make the composition more uniform.

After the healing powder is mixed as above, it is ready to be applied to the flesh wound. First, of course, the wound should be thoroughly washed with a good quality veterinary soap, such as Castille, until the flesh begins to bleed; however, excessive bleeding should be avoided. After the wound has been washed, the mixed healing powder is applied directly onto the wound. Applicant's experience is that the above-described preparation and washing technique enables the healing powder to adhere to the wound to enhance healing. It is Applicant's further experience that repetition of the above procedure twice daily, once in the morning and once in the evening, best promotes healing.

When mixed and used in the above manner, the composition herein disclosed prevents scab formation on the wound and appears to promote healing of the wound from within. The prevention of scab formation likewise prevents scar formation. The use of the healing powder also prevents flies, gnats and other pests from invading the wound area, which also promotes healing, since the animal will not lick at or bite or scratch the wound area as much if it is not being irritated by pests.

While the above-set-forth mixture (i.e., one gallon lime, one-half cup alum and one cup salt) is a good all-purpose mixture which works well in most situations, the composition herein disclosed is effective within a range of compositions. Applicant's experience reveals that as much as two cups and as little of one-fourth cup of alum, and as much as one-and-a-half cups and as little as one-half cup salt can be effectively used. Generally, the above-set-forth basic composition produces acceptable results, but more or less alum or salt may be required depending upon the characteristics of the particular wound.

When more alum is used, this seems to restrict the skin surface bleeding more and this tends to lengthen the overall healing process, since blood flow is more restricted at the surface. When less alum is used, the astringent function of the composition is lessened, and this may also lengthen healing time. When less salt is used, this seems to provide less antiseptic to the curing process, with expected results. When too much salt is used, this stings the animal too much and healing is usually impeded because the animal will not cooperate during application and it will also try to rub or lick off the powder after it has been applied.

After the healing powder has been applied twice daily in the manner described above for a sufficient number of days, the wound will heal. After healing, hair growth can be promoted such as applying a mixture of salt and bacon grease.

It should be understood that while the foregoing discussion has illustrated the use of the disclosed composition pertaining to horses, the disclosed composition is viewed by Applicant as being useful on other livestock as well, such as cows, sheep, hogs, dogs, cats and other domestic and non-domestic animals.

Applicant's experience is that use of the disclosed powder has produced unexpected results, often succeeding where other veterinary treatments have failed. In several instances, conventional healing techniques had failed to heal some particularly severe wounds, and the animal was scheduled for destruction. After applying the disclosed composition to the wound in the disclosed method, the wound healed and the animal was saved.

I claim:

1. Composition for promoting the healing of a wound of an animal, comprising:
   from 82.05 to 95.52 volume percent lime;
   from 1.41 to 10.81 volume percent alum; and
   from 2.70 to 8.45 volume percent salt, which has been well mixed and blended.

2. The composition of claim 1 wherein said lime and said alum are powdered and said salt is granular prior to said mixing and blending.

3. Method of treating exterior wounds in animals to permit healing of said wound from inside out and prevent intrusion or irritation of gnats, flies and other like pests and further prevent formation of scab over said wound, comprising the steps washing said wound with soap until said wound is clean and bleeding has just begun, and applying the composition of claim 1 to said washed wound until said wound heals.

4. The composition of claim 2 wherein the proportion of said powdered lime is from 88.0 to 93.0 volume percent, the proportion of said powdered alum is from 2.5 to 6.0 volume percent, and the proportion of said granulated salt is from 4.0 to 7.0 volume percent.

5. The composition of claim 2 wherein the proportion of said powdered lime is 91.42 volume percent, the proportion of said powdered alum is 2.857 volume percent, and the proportion of said granulated salt is 5.71 volume percent.

6. The composition of claim 2 wherein the proportion of said powdered lime is one gallon, the proportion of said alum is one-half cup, and the proportion of said granulated salt is one cup.

7. The composition of claim 2 wherein said animal being treated is a horse.

8. The method of claim 3 wherein said animal being treated is a horse.

* * * * *